United States Patent [19]

Stupak et al.

[11] Patent Number: 5,162,117
[45] Date of Patent: Nov. 10, 1992

[54] CONTROLLED RELEASE FLUTAMIDE COMPOSITION

[75] Inventors: Elliot Stupak, West Caldwell; W. Philip Cho, Princeton, both of N.J.

[73] Assignee: Schering Corporation, Kenilworth, N.J.

[21] Appl. No.: 796,195

[22] Filed: Nov. 22, 1991

[51] Int. Cl.⁵ .......................... A61K 9/30; A61K 9/24
[52] U.S. Cl. .................................... 424/475; 424/472; 424/474; 424/476; 424/479; 424/480; 424/481; 424/482; 424/465; 424/497
[58] Field of Search ............... 424/464, 465, 497, 472, 424/474, 475, 476, 479, 480, 481, 482

[56] References Cited

U.S. PATENT DOCUMENTS 4,329,364  5/1982  Neri et al. ..................... 424/324
4,474,813  10/1984  Neri et al. ..................... 424/324

FOREIGN PATENT DOCUMENTS 2222947  3/1990  United Kingdom .

Primary Examiner—Thurman K. Page
Assistant Examiner—James M. Spear
Attorney, Agent, or Firm—John J. Maitner; Eric S. Dicker

[57] ABSTRACT

A controlled release solid dosage tablet of flutamide is disclosed that is designed to provide an immediate release dose and a second delayed dose in pulsatile manner in the gastrointestinal tract for twice a day use.

9 Claims, No Drawings

CONTROLLED RELEASE FLUTAMIDE COMPOSITION

BACKGROUND OF THE INVENTION

The present invention relates to pharmaceutical compositions of flutamide. Specifically, the invention relates to a controlled release form which is designed to provide an immediate release dose and a second delayed dose.

U.S. Pat. No. 4,329,364 discloses that flutamide is useful in treating, alleviating and palliation of androgen-caused and/or androgen-dependant conditions such as prostatic hyperplasia, for example benign prostatic hypertrophy and prostatic carcinoma.

U.S. Pat. No. 4,474,813 discloses conventional pharmaceutical preparations of flutamide adapted for systemic administration providing a therapeutic effect against prostatic carcinoma.

Flutamide which has the chemical name 2-methyl-N-[4-nitro-3-(trifluoromethyl)phenyl]propanamide, or N-isobutyryl-4-nitro-3-trifluoromethylanilide, is a nonsteroidal compound devoid of androgenic, adrenocortical, anti-estrogenic, estrogenic, progestational, and antifertility actions. This compound has proved to be a potent antiandrogen and is approved for the palliative treatment of advanced prostate cancer in man. The approved therapeutic dose is 750 mg/day of flutamide in three divided doses of 250 mg/dose. The approved product, Eulixin ®, is available in capsules containing 125 mg of flutamide, therefore, the patient takes two capsules three times a day. Patient compliance with the recommended dosage schedule is sometimes poor, since a large number of patients undergoing this treatment are elderly and are forgetful.

One of the objects of the present invention was to develop a controlled release oral dosage form of flutamide which would allow for twice a day use. In addition, the novel controlled release dosage form would provide comparable bioavailability when compared to the standard capsule dosage form.

DETAILED DESCRIPTION OF THE INVENTION

The present invention provides a controlled release solid dosage form of flutamide. The controlled release dosage form is designed to provide an immediate release dose and a second delayed dose in pulsatile manner in the gastrointestinal tract for twice a day use. The desired release is obtained by forming a core containing a rapidly dissolving solid dispersion of flutamide in a carrier which is capable of forming a solid dispersion with flutamide. The release of flutamide from the core is delayed by coating the core tablet with a barrier or enteric coating. A layer of flutamide is then applied to the coated core tablet to provide the immediate release initial dose.

The core of the novel table formulation provides the second dose of this invention comprising 20 to 80 percent by weight of the total amount of flutamide in the tablet and a carrier capable of forming a solid dispersion with flutamide, said carrier being present in the range of 1:1 to 1:5 parts by weight of the flutamide in the core, and preferably 1:3 parts by weight of flutamide in the core.

Carriers utilized in the core of the tablet are selected from the group consisting of polyethylene glycols, polyvinylpyrrolidones, (molecular weight 10,000 to 360,000), citric acid, succinic acid and bile acid. The preferred carriers are polyethylene glycols which are linear polymers formed by the addition reaction of ethylene oxide. The polyethylene glycols utilized in this invention are solids at room temperature with molecular weights of 1,000 to 20,000. Examples of polyethylene glycols useful in the formulation of this invention are commercially available from Union Carbide Corporation in various grades under the trademark Carbowax ®. A particularly useful polyethylene glycol is Carbowax ® 3350 which has a molecular weight range of 3000 to 3700 and a melting range of 54° to 58° C. This material is also known as PEG-75 according to the Cosmetic, Toilertries and Frangrances Association (CTFA) nomenclature.

The tablet core may also include other auxiliary excipients, such as, diluents, lubricants, glidants and disintegrants.

Examples of diluents that may be utilized in the present invention include: dicalcium phosphate, calcium phosphate, lactose, cellulose, mannitol, sodium chloride, starch, and microcrystalline cellulose. The preferred diluent in the core is microcrystalline cellulose. The diluent comprises from about 15 to 35 percent by weight of the core and preferably 23 percent by weight of the core.

Examples of lubricants that may be utilized in the present invention include talc, magnesium stearate, calcium stearate, stearic acid, hydrogenated vegetable oils and the like. The preferred lubricant in the core is magnesium stearate. The lubricant comprises from about 0.1 to 1.0 percent by weight of the core and preferably 0.26 percent by weight of the core.

Examples of glidants that may be utilized in the present invention include silicon dioxide and talc. The preferred glidant in the core is silicon dioxide. The glidant comprises from about 0.5 to 2.0 percent by weight of the core and preferably 1.33 percent by weight of the core.

Examples of disintegrants that may be utilized in this invention include starches, celluloses, algins, gums, cross-linked polymers, such as croscarmellose sodium (a crosslinked polymer of carboxymethylcellulose sodium), crospovidone and the like. The preferred disintegrant in the core is the croscarmellose sodium. The disintegrant comprises from about 4 to 12 percent by weight of the core, preferably 8 percent by weight of the core.

The core component of the tablet of this invention is coated with an enteric coating material. The enteric coating resists solution in gastric fluid but disintegrates and dissolves in the intestine. The enteric coating comprises 4 to 15 percent by weight of the core, and preferably 6 to 12 percent by weight of the core. Examples of enteric coatings that may be utilized in the present invention include polyvinyl acetate phthalate, methacrylic acid copolymer, hydroxypropyl methylcellulose phthalate, hydroxypropyl methylcellulose acetate succinate, cellulose acetate phthalate, cellulose acetate succinate and cellulose acetate trimellitate.

The preferred enteric coating material is polyvinyl acetate phthalate (PVAP). This enteric coating is produced by the esterification of a partially hydrolyzed polyvinyl acetate with phthalic anhydride. The acetate polymer is low molecular weight and 87 to 89 mole percent hydrolyzed. An example of a PVAP preparation useful in the formulation of this invention is commercially available from Colorcon, Inc., West Point, Pa.

The immediate release initial dose component of the tablet of the present invention contains flutamide. The amount of flutamide present in the immediate release outer coating is 80 to 20 percent of the total amount of flutamide in the tablet. The amount of immediate dose flutamide is applied to the enteric coated core as a dusting powder. The flutamide may be combined with auxiliary excipients, such as the excipients utilized in preparing the core of this invention. Examples of such excipients include lactose, croscarmellose sodium, sodium lauryl sulfate, calcium sulfate, microcrystalline cellulose and acacia which is utilizied as a binder.

In preparing the tablet of the invention, conventional tabletting techniques are employed to prepare the core component. For example, dry granulation, wet granulation or direct compression can be used to prepare the core. One method for manufacturing the core for the tablet of this invention involves forming a solid dispersion by melting the carrier material and dissolving the flutamide in the melted carrier material. After the solid dispersion solidifies, the dispersion is milled using conventional milling equipment. Any other ingredients such as diluents (e.g. microcrystalline cellulose), disintegrants (e.g. sodium croscarmellose), glidants (e.g. silicon dioxide), lubricants (e.g. magnesium stearate) and the like are added to the milled solid dispersion material, mixed and compressed into a suitable size and shape using conventional tabletting machines.

The core material is then coated with an enteric coating known to those skilled in the art (e.g. polyvinyl acetate phthalate) using conventional coating techniques.

The immediate release dose of flutamide is then applied as a dusting powder to the enteric coated core. The flutamide dusting powder is prepared by blending flutamide with excipients such as lactose, croscarmellose sodium and sodium lauryl sulfate in a suitable mixer. The enteric coated cores are coated with the flutamide dusting powder using a binder (e.g. acacia) with suitable coating equipment. The tablets may then be used as is or they can be film, sugar and color coated by techniques well known in the art.

The following examples described typical tablet formulations, dissolution profiles and a bioavailability study of the controlled release dosage forms of the present invention, but are not to be interpreted as limiting the scope of the appended claims in any way.

EXAMPLE 1

A controlled release tablet was prepared from the following ingredients:

| INGREDIENTS | MG/TABLET |
| --- | --- |
| Core Tablet | |
| Flutamide | 75 |
| Polyethylene Glycol 3350 | 225 |
| Microcrystalline Cellulose | 106.8 |
| Sodium Croscarmellose | 36 |
| Silicon Dioxide | 6 |
| Magnesium Stearate | 1.2 |
| Approximate Core Tablet Weight | 450 |
| Coating | |
| Flutamide | 112.5 |
| Polyvinyl Acetate Phthalate | 45 |
| HPMC/PEG Clear Solution (Solids) | 6.75 |
| Hydrous Lactose | 28.9 |
| Sodium Croscarmellose | 16.1 |
| Sodium Lauryl Sulfate | 3.2 |
| Calcium Sulfate | 220 |
| Acacia | 27 |
| Butylparaben | 0.03 |
| Sugar | 200 |
| Dye Color Dispersion (Solids) | 14 |
| White Wax | 0.3 |
| Carnauba Wax | 0.3 |
| Approximate Coating Weight | 674 |
| Approximate Coated Tablet Weight | 1124 |

Preparation of the tablet is as follows:

Core:

A solid dispersion was prepared by melting the polyethylene glycol in a suitable size container. The flutamide was dissolved in the melted polyethylene glycol and the solid dispersion was allowed to solidify. The solid dispersion was milled using a suitable size screen. The flutamide solid dispersion was blended with the microcrystalline cellulose, sodium croscarmellose, silicon dioxide and magnesium stearate in a suitable mixer. The blended material was compressed into a suitable size and shape core tablet.

B. Enteric and Active Coatings:

The cores were coated with an enteric material (e.g. polyvinyl acetate phthalate) in a suitable coating pan. A precoat and/or overcoat of HPMC/PEG may be applied if desired. A flutamide dusting powder was prepared by blending flutamide, lactose, croscarmellose sodium and sodium lauryl sulfate in a suitable mixer. The enteric coated cores were coated with the flutamide dusting powder using acacia as binder in a suitable coating pan. The tablets may then coated with a film coat, sugar coat or color coat using standard procedures. The coated tablets can be polished using the wax solutions.

Release rates of the tablet of this example were determined using U.S.P. paddle method (as described in U.S.P. XXII) at 75 revolutions per minute in 1000 ml of 0.05 sodium phosphate monobasic in 3% SLS, pH 3.0. After the second hour 5.0 ml of 15% sodium hydroxide was added to provide a pH 6. A typical profile is shown below:

| In-Vitro Tablet Dissolution | |
| --- | --- |
| Time (hour) | Percent Dissolved |
| 2 | 60 |
| 3 | 102 |
| 4 | 101 |

EXAMPLE 2

A controlled release tablet was prepared from the following ingredients:

| INGREDIENTS | MG/TABLET |
| --- | --- |
| Core Tablet | |
| Flutamide | 75 |
| Polyethylene Glycol 3350 | 225 |
| Microcrystalline Cellulose | 106.8 |
| Sodium Croscarmellose | 36 |
| Silicon Dioxide | 6 |
| Magnesium Stearate | 1.2 |
| Approximate Core Tablet Weight | 450 |
| Coating | |

| INGREDIENTS | MG/TABLET |
|---|---|
| Flutamide | 112.5 |
| Polyvinyl Acetate Phthalate | 27 |
| HPMC/PEG Clear Solution (Solids) | 40 |
| Hydrous Lactose | 28.9 |
| Sodium Croscarmellose | 16.1 |
| Sodium Lauryl Sulfate | 3.2 |
| Calcium Sulfate | 77.4 |
| Acacia | 25.9 |
| Butylparaben | 0.03 |
| Sugar | 103.5 |
| Approximate Coating Weight | 435 |
| Approximate Coated Tablet Weight | 885 |

The tablet was prepared according to the procedure of Example 1.

Release rates of the tablet of this example were determined using U.S.P. paddle method (as described in U.S.P. XXII) at 75 revolutions per minute in 1000 ml of 0.05 sodium phosphate monobasic in 3% SLS, pH 3.0. After the second hour 5.0 ml of 15% sodium hydroxide was added to provide a pH 6. A typical profile is shown below:

| In-Vitro Tablet Dissolution | |
|---|---|
| Time (hour) | Percent Dissolved |
| 2 | 58 |
| 3 | 98 |
| 4 | 101 |

The tablets of the above example were tested in a randomized, open-label four-way crossover design wherein the volunteers received each of the following treatments:

Treatment A: Two 125 mg flutamide conventional capsules (Eulixin ®-Schering Labs) at 8 a.m., 4 p.m. and 12 midnight.

Treatment B: Two 187.5 mg tablets of the above example at 8 a.m. and 8 p.m.

Results of the study demonstrated comparable bioavailability (area under the curve-AUC) between the Eulixin ® capsule and the tablets of this invention.

We claim:

1. A controlled release flutamide tablet comprising:
   (a) a core which comprises 20 to 80 percent by weight of the total weight of flutamide in the tablet and a carrier capable of forming a solid dispersion with flutamide, said carrier being present in the range of 1:1 to 1:5 parts by weight of the flutamide in the core;
   (b) 4 to 15 percent by weight of the core of an enteric coating material; and
   (c) 80 to 20 percent by weight of the total amount of flutamide in the tablet is present in the immediate release outer coating.

2. The controlled release tablet of claim 1 wherein the carrier material in the core is selected from the group consisting of polyethylene glycol, polyvinylpyrrolidone, citric acid, succinic acid and bile acid.

3. The controlled release tablet of claim 1 wherein the carrier material in the core is polyethylene glycol.

4. The controlled release tablet of claim 1 wherein the range of carrier present in the core is 1:3 by weight of the flutamide in said core.

5. The controlled release tablet of claim 1 wherein the enteric coating is selected from the group consisting of polyvinyl acetate phthalate, methacrylic acid copolymer, hydroxypropyl methylcellulose phthalate and hydroxypropyl, methylcellulose acetate succinate, cellulose acetate phthalate, cellulose acetate succinate and cellulose acetate trimellitate.

6. The controlled release tablet of claim 5 wherein the enteric coating is polyvinyl acetate phthalate.

7. A controlled release flutamide tablet which comprises:
   (a) a core comprising:
      20 to 80 percent by weight of the total weight of flutamide in the tablet and a carrier capable of forming a solid solution with flutamide, said carrier being present in the range of 1:1 to 1:5 parts by weight of the flutamide in the core;
      15 to 35 percent by weight of the core of a diluent;
      0.1 to 1 percent by weight of the core of a lubricant;
      0.5 to 2 percent by weight of the core of a glidant;
      4 to 12 percent by weight of the core of a disintegrant;
   (b) 4 to 15 percent by weight of the core of an enteric coating; and
   (c) 80 to 20 percent by weight of total amount of flutamide in the tablet is present in the immediate release outer coating.

8. A controlled release tablet comprising:

| INGREDIENTS | MG/TABLET |
|---|---|
| Core Tablet | |
| Flutamide | 75 |
| Polyethylene Glycol 3350 | 225 |
| Microcrystalline Cellulose | 106.8 |
| Sodium Croscarmellose | 36 |
| Silicon Dioxide | 6 |
| Magnesium Stearate | 1.2 |
| Approximate Core Tablet Weight | 450 |
| Coating | |
| Flutamide | 112.5 |
| Polyvinyl Acetate Phthalate | 45 |
| HPMC/PEG Clear Solution (Solids) | 6.75 |
| Hydrous Lactose | 28.9 |
| Sodium Croscarmellose | 16.1 |
| Sodium Lauryl Sulfate | 3.2 |
| Calcium Sulfate | 220 |
| Acacia | 27 |
| Butylparaben | 0.03 |
| Sugar | 200 |
| Dye Opulux White (Solids) | 14 |
| White Wax | 0.3 |
| Carnauba Wax | 0.3 |
| Approximate Coating Weight | 674 |
| Approximate Coated Tablet Weight | 1124 |

9. A controlled release tablet comprising:

| INGREDIENTS | MG/TABLET |
|---|---|
| Core Tablet | |
| Flutamide | 75 |
| Polyethylene Glycol 3350 | 225 |
| Microcrystalline Cellulose | 106.8 |
| Sodium Croscarmellose | 36 |
| Silicon Dioxide | 6 |
| Magnesium Stearate | 1.2 |
| Approximate Core Tablet Weight | 450 |
| Coating | |
| Flutamide | 112.5 |
| Polyvinyl Acetate Phthalate | 27 |
| HPMC/PEG Clear Solution (Solids) | 40 |
| Hydrous Lactose | 28.9 |
| Sodium Croscarmellose | 16.1 |
| Sodium Lauryl Sulfate | 3.2 |
| Calcium Sulfate | 77.4 |
| Acacia | 25.9 |
| Butylparaben | 0.03 |
| Sugar | 103.5 |
| Approximate Coating Weight | 435 |
| Approximate Coated Tablet Weight | 885 |

* * * * *